US009029619B2

(12) United States Patent
Vermeiren (10) Patent No.: US 9,029,619 B2
(45) Date of Patent: May 12, 2015

(54) PROCESS TO MAKE ALPHA OLEFINS FROM ETHANOL

(75) Inventor: Walter Vermeiren, Houthalen (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 459 days.

(21) Appl. No.: 13/133,018

(22) PCT Filed: Dec. 10, 2009

(86) PCT No.: PCT/EP2009/066812
§ 371 (c)(1),
(2), (4) Date: Aug. 1, 2011

(87) PCT Pub. No.: WO2010/066830
PCT Pub. Date: Jun. 17, 2010

(65) Prior Publication Data
US 2011/0288256 A1      Nov. 24, 2011

(30) Foreign Application Priority Data

Dec. 11, 2008   (EP) ..................................... 08171315

(51) Int. Cl.
*C08F 210/02* (2006.01)
*C07C 11/08* (2006.01)
*C07C 11/107* (2006.01)

(52) U.S. Cl.
CPC ............... *C07C 11/08* (2013.01); *C07C 11/107* (2013.01)

(58) Field of Classification Search
CPC .................................... C07C 6/02; C07C 6/04
USPC ......... 585/638, 639, 477, 478, 479, 480, 481, 585/482, 310, 330, 640, 641, 642, 502, 520, 585/523, 527, 531
See application file for complete search history.

(56) References Cited

U.S. PATENT DOCUMENTS 5,221,775 A    6/1993 Wu (Continued)

FOREIGN PATENT DOCUMENTS

DE         1643995 A1    7/1971

OTHER PUBLICATIONS

Talukdar et al. "1-Hexene Isomerization and n-Hexane Cracking over HMCM-22." Applied Catalysis A: General 213 (20011) 239-245.*
P. Tynjl, Pakkanen, T., Mustamki, S.: Journal of Physical Chemistry B, 1998, pp. 5280-5286, vol. 102.

(Continued)

*Primary Examiner* — In Suk Bullock
*Assistant Examiner* — Sharon Pregler

(57) ABSTRACT

The present invention relates to a process to make alpha olefins comprising:
  dehydrating ethanol to recover an ethylene stream,
  introducing said ethylene stream into an oligomerization zone containing an oligomerization catalyst and into contact with said oligomerization catalyst,
  operating said oligomerization zone at conditions effective to produce an effluent consisting essentially of 1-butene, 1-hexene, optionally heavier alpha olefins and unconverted ethylene if any,
  introducing the above effluent into a fractionation zone to recover a stream consisting essentially of 1-butene, a stream consisting essentially of 1-hexene, optionally a stream consisting essentially of heavier alpha olefins and an optional ethylene stream.

In an advantageous embodiment the 1-hexene or at least one heavier alpha olefins, if any, are isomerized to an internal olefin and subsequently transformed by metathesis with the aid of additional ethylene into different alpha-olefins with even or odd number of carbons. By way of example 1-hexene is isomerized into 2-hexene and by methathesis with ethylene converted to 1-pentene and propylene.

In another embodiment the oligomerization zone is only a dimerization zone and butene is produced. 1-butene is isomerized to 2-butene and sent to a methathesis zone in the presence of ethylene to be converted to propylene. In said embodiment the dehydration catalyst is selected in the group consisting of a crystalline silicate having a ratio Si/Al of at least about 100, a dealuminated crystalline silicate, and a phosphorus modified zeolite.

21 Claims, 5 Drawing Sheets

(56) References Cited

U.S. PATENT DOCUMENTS

| | | | |
|---|---|---|---|
| 5,292,979 A | 3/1994 | Chauvin et al. | |
| 6,777,582 B2 * | 8/2004 | Gartside et al. | 585/324 |
| 2003/0078463 A1 * | 4/2003 | Martens et al. | 585/638 |
| 2004/0138512 A1 * | 7/2004 | Roper et al. | 585/643 |
| 2008/0154078 A1 * | 6/2008 | Bozzano et al. | 585/324 |
| 2009/0299109 A1 * | 12/2009 | Gruber et al. | 585/240 |

OTHER PUBLICATIONS

Le Van Mao, R et al: "Conversion of Ethanol in Aqueous Solution over ZSM-5 Zeolites", Applied Catalysis, Jan. 1, 1990, pp. 131-173, vol. 61, Amsterdam, NL.

Le Van Mao, Raymond et al: "Bioethanol-to-ethylene (B.E.T.E.) process", Applied Catalysis, Mar. 15, 1989, pp. 265-277, vol. 48, No. 2.

* cited by examiner

PROCESS TO MAKE ALPHA OLEFINS FROM ETHANOL

CROSS-REFERENCE TO RELATED APPLICATIONS

This application claims the benefit of PCT/EP2009/066812, filed Dec. 10, 2009, which claims priority from EP 08171315.8, filed Dec. 11, 2008.

FIELD OF THE INVENTION

The present invention relates to the transformation of ethanol from biological origin into linear alpha-olefins. The invention consists in the dehydration of ethanol into ethylene and subsequent dimerisation or oligomerisation optionally combined with isomerisation and metathesis.

There is an increased demand for the production of petrochemicals from biological origin in order to respond to the decreasing crude oil supply and the increasing crude oil price or production cost and to respond to the need to make petrochemicals from non-fossil hydrocarbons in order to minimise the net emission of fossil $CO_2$ into the atmosphere. Petrochemicals from biological origin are generally considered as renewable as the eventual emitted $CO_2$ at the end of its life cycle is used again by vegetation in order to produce new biomass.

Bio-ethanol production by fermentation of carbohydrates or by catalytic synthesis from synthesis gas (a mixture of CO and $H_2$) made by gasification of biomass can be transformed into ethylene by means of acidic solid catalysts.

The object of the present invention is the production of alpha-olefins from ethanol from biological origin. The invention involves the acid catalysed dehydration of ethanol into ethylene; the ethylene is subsequently dimerised or oligomerised into alpha-olefins, exhibiting an even number of carbons. This invention allows to produce 1-butene, 1-hexene, 1-octene, 1-decene, 1-dodecene and higher alpha-olefins. In another embodiment of the present invention, the dimeric or oligomeric alpha-olefins are transformed into internal olefins that are subsequently transformed by metathesis with the aid of additional ethylene into different alpha-olefins with even or odd number of carbons. Beside the above-mentioned even numbered alpha-olefins, the present invention allows also to produce odd numbered alpha-olefins like propylene, 1-pentene, 1-heptene, 1-nonene etc.

Alpha-olefins are used in order of importance as comonomer for polyethylene (mainly 1-butene and 1-hexene), plastomers (mainly 1-octene), for linear alkyl-benzene, detergent and plasticizer alcohols, sulfonates, amines, mercaptans, poly-alpha-olefins and poly-1-butene.

The present invention allows producing alpha-olefins from biological origin that can be used for polyethylene production. Especially LLDPE and HDPE production require significant amounts of alpha-olefins in order to control the density, mechanical and processing properties. Typically, between 1 to 10 wt % of the final polymers consist of the alpha-olefin.

BACKGROUND OF THE INVENTION

U.S. Pat. No. 5,292,979 describes a process for the conversion of ethylene into light alpha-olefins comprising contacting ethylene with at least one catalyst obtained by the reaction of a preformed mixture of alkyl zirconate and ether, in an ether/zirconate molar ration of 0.5:1 to 10:1, with at least one aluminium compound of general formula $AlR_nX_{3-n}$, in which R is a hydrocarbyl radical, X is a chlorine or bromine atom and n is 1-2.

U.S. Pat. No. 5,157,190 describes a process for making higher alpha-olefins from ethylene by chain growth comprising the steps of feeding ethylene and an alkyl aluminium compound to a reaction zone maintained under chain growth conditions to produce tri-alkyl aluminium compounds, feeding at least a part of said tri-alkyl aluminium compounds and butene as reactants to a displacement zone maintained under displacement conditions to form a butene displacement product comprising mainly tri-butyl aluminium, ethylene and alpha-olefins and conveying the tri-butyl aluminium to a chain growth zone fed with additional ethylene.

EP257232 describes a process for oligomerising ethylene to normal alpha-olefins and recovering said olefins from the reaction product, which comprises reaction ethylene in a methanol-water mixture containing 0.5-20 wt % water under oligomerisation conditions in contact with a nickel ylide catalyst.

U.S. Pat. No. 4,487,847 describes a novel ethylene dimerisation catalyst to make 1-butene. Said catalyst consists of a nickel compound, a phosphine compound, and an acidic compound in an effective solvent at a temperature from about 0° C. to about 200° C.

EP135441 describes an improved process for converting ethylene to 1-butene, wherein ethylene is contacted with a catalyst obtained by reacting an alkyl titanate with an alkyl aluminium compound, characterised in that said catalyst results from reacting a preformed mixture of alkyl titanate and ether, in a molar ratio ether/titanate form 0.5:1 to 10:1, with an aluminium compound of formula $AlR_3$ or $AlR_2H$, wherein each R is a hydrocarbyl radical.

U.S. Pat. No. 5,221,775 describes an ethylene dimerisation process wherein ethylene is contacted with an organonickel (0) compound and a phosphine compound in a fluorinated alcohol solvent to produce a precursor reaction mixture, followed by contacting ethylene with the precursor reaction mixture and a fluorinated organoacid to produce a product reaction mixture comprising a C4 fraction of predominantly 2-butenes.

U.S. Pat. No. 5,672,802 teaches a process for the preparation of an alpha-olefin product having a narrow molecular weight range which comprises metathesizing an internal olefin under non-equilibrium conditions and thereby producing a lower boiling internal olefin product which is removed as formed, and a high boiling mid-chain internal olefin product, thereafter contacting and reaction the high boiling mid-chain internal olefin product with ethylene to produce an alpha-olefin product having a narrow molecular weight range.

EP803490 describes a process for the conversion of ethylene to but-1-ene, wherein, in a reaction enclosure, the ethylene is brought into contact with a solution of a catalyst resulting from the interaction of at least one alkyl titanate with at least one aluminium compound of the formula $AlR_3$ or $AlR_2H$, each of the residues R being a hydrocarbyl radical, the process being characterised in that it takes place in the presence of at least one additive selected from the group formed by quaternary ammonium salts.

In US 2001/0023281 a process to produce 1-hexene is described wherein a catalytic composition is obtained by mixing at least one chromium compound with at least one aryloxy compound of an element M selected from the group formed by magnesium, calcium, strontium and barium, with general formula $M(RO)_{2-n}X_n$ where RO is an aryloxy radical containing 6 to 80 carbon atoms, X is a halogen or a hydrocarbyl radical containing 1 to 30 carbon atoms and n is a whole number that can take values of 0 to 2, and with at least one aluminium compound selected from hydrocarbylaluminum compounds (tris(hydrocarbyl)-aluminum, chlorinated or brominated hydrocarbylaluminum compounds) and aluminoxanes. The catalytic composition can be used in an ethylene oligomerisation process, in particular to produce 1-hexene.

U.S. Pat. No. 5,198,563 describes a catalyst for producing in particular 1-hexene whereas novel chromium-containing compounds, such as, for example, chromium pyrrolides, are prepared by forming a mixture of a chromium salt, a metal amide, and an electron pair donor solvent, such as, for example, an ether. These novel chromium-containing, or chromium pyrrolide, compounds can be used either unsupported or supported on an inorganic oxide support to trimerize and/or polymerize olefins.

In all the above prior arts ethylene is not originating from ethanol.

In U.S. Pat. No. 7,223,895 an ethane or other hydrocarbon feedstock is steam cracked to produce an ethylene stream which is processed in an ethylene plant recovery section to separate an ethane recycle and a polymer grade or chemical grade ethylene product stream. A portion of the ethylene product stream may then be reacted by dimerization to produce a butene stream. These formed butenes and/or butenes recovered from other sources and another portion of the ethylene product stream are reacted by metathesis to produce a propylene stream which is deethanized and separated from heavier hydrocarbons to produce the propylene product. The butene product stream may also be deethanized and is separated from heavier hydrocarbons. The overhead from the metathesis section deethanizer may be recycled to the ethylene plant recovery section. The reflux for the metathesis section deethanizer may be generated from the overhead or may be a portion of the ethylene product stream. In said prior art ethylene is not originating from ethanol and has to be purified by a selective hydrogenation to remove acetylene.

US20070112236 describes an integrated method that comprises an ethane thermal cracking operation to form at least ethylene, coupled with dimerization and metathesis operations, the dimerization operation forming butene for the metathesis operation, and the metathesis operation forming additional amounts of propylene. In said prior art ethylene is not originating from ethanol and has to be purified by a selective hydrogenation to remove acetylene.

US20070203384 describes a process for producing light olefins from an oxygenate-containing feedstock, said process comprising:

contacting the oxygenate-containing feedstock in an oxygenate conversion reactor with an oxygenate conversion catalyst and at reaction conditions effective to convert the oxygenate-containing feedstock to an oxygenate conversion effluent stream comprising light olefins and $C_4$+ hydrocarbons, wherein the light olefins comprise ethylene and the $C_4$+ hydrocarbons comprise a quantity of butenes including a quantity of 1-butenes; treating the oxygenate conversion effluent stream and forming a first process stream comprising at least a portion of the quantity of butenes including 1-butenes from the oxygenate conversion effluent stream;

isomerizing at least a portion of the quantity of 1-butenes of the first process stream to form an isomerized stream comprising a quantity of 2-butenes;

contacting at least a portion of the quantity of 2-butenes of the isomerized stream with ethylene in a metathesis zone at effective conditions to produce a metathesis effluent stream comprising propylene; and recovering propylene from the metathesis effluent stream. In said prior art ethylene is not originating from ethanol.

WO2007083241 relates to a production method for propylene characterized in that ethanol is converted into propylene by continuously reacting ethanol on a catalyst. More precisely the ethanol is converted into the propylene by:

forming ethylene through a dehydration reaction between the catalyst and the ethanol;

forming a butyl cation through a dimerization reaction between the ethylene formed and an ethyl cation obtained from the catalyst;

forming a butene from the butyl cation;

forming a carbocation through a trimerization reaction between the butene and the ethyl cation; and forming propylene through a cleavage reaction of the carbocation.

The catalysts for the dehydration, dimerisation, trimerisation and cleavage reaction is a solid acid. There are no examples describing clearly an ethanol feedstock, a catalyst, a reactor, operating conditions and the composition of the effluent deemed to comprise propylene.

EP1953129 A1 (=WO 2007-055361) explains that ethanol obtained from ordinary biomass resources contains many impurities other than water and these impurities themselves or their decomposition products contaminate ethylene when the ethylene is produced by a dehydration reaction, whereby the activity of metathesis catalyst is adversely affected. According to EP1953129 A1 a method for producing propylene is characterized in that the ethanol obtained from biomass is converted to ethylene by a dehydration reaction, the ethylene is separated from the generated water, the separated ethylene is purified by adsorption in an adsorption tower filled with an adsorbent, and then a metathesis reaction is carried out along with a raw material containing n-butene. Optionally said butene is made by dimerization of ethylene obtained by dehydration of ethanol. As a consequence propylene having biomass-derived carbon and reduced-environmental burden can be produced without lowering the catalysis activity.

BRIEF SUMMARY OF THE INVENTION

The present invention relates to a process to make alpha olefins comprising:
a) providing a dehydration zone containing a dehydration catalyst,
b) introducing a feedstock comprising ethanol, optionally water, optionally an inert component into said dehydration zone and into contact with said dehydration catalyst,
c) operating said dehydration zone at conditions effective to dehydrate at least a portion of the ethanol to essentially ethylene,
d) recovering from step c) an effluent comprising essentially ethylene, water, unconverted ethanol if any and the optional inert component,
e) introducing said effluent into a fractionation zone to recover an ethylene stream,
f) introducing said ethylene stream into an oligomerization zone containing an oligomerization catalyst and into contact with said oligomerization catalyst,
g) operating said oligomerization zone at conditions effective to produce an effluent consisting essentially of 1-butene, 1-hexene, optionally heavier alpha olefins and unconverted ethylene if any,
h) introducing the effluent from step g) into a fractionation zone to recover a stream consisting essentially of 1-butene, a stream consisting essentially of 1-hexene, optionally a stream consisting essentially of heavier alpha olefins and an optional ethylene stream. In the above sentence "heavier alpha olefins" means alpha olefins having 8 carbons or more.

In an advantageous embodiment:
the oligomerization of step g) is operated at conditions effective to produce an effluent consisting essentially of 1-butene, 1-hexene, 1-octene, optionally heavier alpha olefins and unconverted ethylene if any, and
in step h) are recovered a stream consisting essentially of 1-butene, a stream consisting essentially of 1-hexene, a stream consisting essentially of 1-octene, optionally a stream consisting essentially of heavier alpha olefins and an optional ethylene stream. In the above sentence "heavier alpha olefins" means alpha olefins having 10 carbons or more and preferably from 10 to 30 carbon atoms.

In an advantageous embodiment the dehydration catalyst is selected in the group consisting of a crystalline silicate having a ratio Si/Al of at least about 100, a dealuminated crystalline silicate, and a phosphorus modified zeolite.

In another advantageous embodiment the optional ethylene stream recovered at step h) is recycled back to the oligomerization zone of step f).

In an advantageous embodiment the 1-hexene or at least one heavier alpha olefins, if any, recovered at step h) are isomerized to an internal olefin and subsequently transformed by metathesis with the aid of additional ethylene into different alpha-olefins with even or odd number of carbons. By way of example 1-hexene is isomerized into 2-hexene and by methathesis with ethylene converted to 1-pentene and propylene.

The present invention relates in a second embodiment to a process to make alpha olefins comprising:
a) providing a dehydration zone containing a dehydration catalyst selected in the group consisting of a crystalline silicate having a ratio Si/Al of at least about 100, a dealuminated crystalline silicate, and a phosphorus modified zeolite,
b) introducing a feedstock comprising ethanol, optionally water, optionally an inert component into said dehydration zone and into contact with said dehydration catalyst,
c) operating said dehydration zone at conditions effective to dehydrate at least a portion of the ethanol to essentially ethylene,
d) recovering from step c) an effluent comprising essentially ethylene, water, unconverted ethanol if any and the optional inert component,
e) introducing said effluent into a fractionation zone to recover an ethylene stream,
f) introducing said ethylene stream into a dimerization zone containing a dimerization catalyst and into contact with said dimerization catalyst,
g) operating said dimerization zone at conditions effective to produce an effluent consisting essentially of 1-butene, optionally heavier alpha olefins and unconverted ethylene if any,
h) introducing the effluent from step g) into a fractionation zone to recover a stream consisting essentially of 1-butene, optionally a stream consisting essentially of heavier olefins and an optional ethylene stream.

In an advantageous embodiment the optional ethylene stream recovered at step h) is recycled back to the dimerization zone of step f).

In another advantageous embodiment there are additional steps comprising:
i) isomerizing the stream consisting essentially of 1-butene recovered at step h) to a stream comprising an increased quantity of 2-butene and advantageously consisting essentially of 2-butene,
j) introducing the effluent comprising 2-butene, recovered from the previous step, into a methathesis zone containing a methathesis catalyst and into contact simultaneously with ethylene and said methathesis catalyst, wherein, the methathesis zone is operated at conditions effective to produce propylene,
k) introducing the effluent of step j) into a fractionation zone to recover propylene, unreacted ethylene, unreacted 2-butene and heavier components,
l) optionally recycling the unreacted ethylene and unreacted 2-butene to the methathesis zone.

The present invention relates in a third embodiment to a process to make alpha olefins comprising:
a) providing a dehydration zone containing a dehydration catalyst selected in the group consisting of a crystalline silicate having a ratio Si/Al of at least about 100, a dealuminated crystalline silicate, and a phosphorus modified zeolite,
b) introducing a feedstock comprising ethanol, optionally water, optionally an inert component into said dehydration zone and into contact with said dehydration catalyst,
c) operating said dehydration zone at conditions effective to dehydrate at least a portion of the ethanol to essentially ethylene,
d) recovering from step c) an effluent comprising essentially ethylene, water, unconverted ethanol if any and the optional inert component,
e) introducing said effluent into a fractionation zone to recover an ethylene stream,
f) introducing said ethylene stream into a dimerization zone containing a dimerization catalyst and into contact with said dimerization catalyst,
g) operating said dimerization zone at conditions effective to produce an effluent consisting essentially of 2-butene, optionally heavier alpha olefins and unconverted ethylene if any,
h) introducing the effluent from step g) into a fractionation zone to recover a stream consisting essentially of 2-butene, optionally a stream consisting essentially of heavier olefins and an optional ethylene stream.

In an advantageous embodiment the optional ethylene stream recovered at step h) is recycled back to the dimerization zone of step f).

In another advantageous embodiment there are additional steps comprising:
i) introducing said 2-butene into a methathesis zone containing a methathesis catalyst and into contact simultaneously with ethylene and said methathesis catalyst, wherein, the methathesis zone is operated at conditions effective to produce propylene,
j) introducing the effluent of step i) into a fractionation zone to recover propylene, unreacted ethylene, unreacted 2-butene and heavier components,
k) optionally recycling the unreacted ethylene and unreacted 2-butene to the methathesis zone.

The present invention relates in a fourth embodiment to a process to make alpha olefins comprising:
a) providing a dehydration zone containing a dehydration catalyst selected in the group consisting of a crystalline silicate having a ratio Si/Al of at least about 100, a dealuminated crystalline silicate, and a phosphorus modified zeolite,
b) introducing a feedstock comprising ethanol, optionally water, optionally an inert component into said dehydration zone and into contact with said dehydration catalyst,
c) operating said dehydration zone at conditions effective to dehydrate at least a portion of the ethanol to essentially ethylene,
d) recovering from step c) an effluent comprising essentially ethylene, water, unconverted ethanol if any and the optional inert component,
e) introducing said effluent into a fractionation zone to recover an ethylene stream, f) introducing said ethylene stream into a trimerization zone containing a trimerization catalyst and into contact with said trimerization catalyst, g) operating said trimerization zone at conditions effective to produce an effluent consisting essentially of 1-hexene, optionally light-ends, heavier alpha olefins and unconverted ethylene if any, h) introducing the effluent from step g) into a fractionation zone to recover a stream consisting essentially of 1-hexene, optionally a stream consisting essentially of heavier olefins and an optional ethylene stream.

In another advantageous embodiment the optional ethylene stream recovered at step h) is recycled back to the trimerization zone of step f).

In all the above first, second, third and fourth embodiments advantageously the ethanol is from biological origin, as a consequence the alpha-olefins are from biological origin.

The propylene, from biological origin, made according to the present invention is further polymerized to polypropylene optionally with one or more comonomers, from biological origin, also made according to the present invention.

The ethylene, from biological origin, made according to the present invention is further polymerized to polyethylene copolymers with one or more comonomers, from biological origin, also made according to the present invention.

The present invention also relates to polyethylene copolymers made from any ethylene and from alpha olefins from biological origin made according to the present invention. Advantageously in the polyethylene copolymers the ethylene is from fossil origin and there are between 0.1 and 15 w % of biological origin alpha-olefins.

The present invention also relates to polyethylene copolymers made from ethylene and alpha olefins wherein at least 1% of the ethylene and 1% of the alpha-olefins are from biological origin and made according to the present invention.

The present invention also relates to polypropylene where the propylene is at least 1% made from biological origin according to the present invention.

The advantage of the ethylene obtained by ethanol dehydration is the absence of acetylene as compared with ethylene produced by steam cracking of naphtha or ethane.

DETAILED DESCRIPTION OF THE INVENTION

First Embodiment of the Invention

As regards the ethanol feedstock, the inert component is any component provided there is no adverse effect on the catalyst. Because the dehydration is endothermic the inert component can be used to bring energy. By way of examples the inert component is selected among the saturated hydrocarbons having up to 10 carbon atoms, naphthenes, nitrogen and CO2. Advantageously it is a saturated hydrocarbon or a mixture of saturated hydrocarbons having from 3 to 7 carbon atoms, more advantageously having from 4 to 6 carbon atoms and is preferably pentane. An example of inert component can be any individual saturated compound, a synthetic mixture of the individual saturated compounds as well as some equilibrated refinery streams like straight naphtha, butanes etc. Advantageously the inert component is a saturated hydrocarbon having from 3 to 6 carbon atoms and is preferably pentane. The weight proportions of respectively alcohol, water and inert component are, for example, 5-100/0-95/0-95 (the total being 100). The ethanol feedstock can be liquid or gaseous.

As regards the dehydration zone, it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

As regards the pressure of the dehydration zone, it can be any pressure but it is more easy and economical to operate at moderate pressure. By way of example the pressure of the dehydration zone ranges from 0.5 to 30 bars absolute (50 kPa to 3 MPa), advantageously from 0.5 to 5 bars absolute (50 kPa to 0.5 MPa), more advantageously from 1.2 to 5 bars absolute (0.12 MPa to 0.5 MPa) and preferably from 1.2 to 4 bars absolute (0.12 MPa to 0.4 MPa). Advantageously the partial pressure of the alcohol is from 1.2 to 4 bars absolute (0.12 MPa to 0.4 MPa), more advantageously from 1.2 to 3.5 bars absolute (0.35 MPa), preferably from 1.2 to 2 bars absolute (0.12 MPa to 0.2 MPa).

As regards the temperature of the dehydration zone, it ranges from 280° C. to 500° C., advantageously from 280° C. to 450° C., more advantageously from 300° C. to 400° C. and preferably from 330° C. to 380° C.

These reaction temperatures refer substantially to average catalyst bed temperature. The ethanol dehydration is an endothermic reaction and requires the input of reaction heat in order to maintain catalyst activity sufficiently high and shift the thermodynamic equilibrium to sufficiently high conversion levels.

In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the alcohol, it ranges advantageously from 2 to 20 $h^{-1}$, more advantageously from 4 to 20 $h^{-1}$, preferably from 5 to 15 $h^{-1}$, more preferably from 7 to 12 $h^{-1}$.

As regards the dehydration catalyst, it can be any acid catalyst capable to cause the dehydration of ethanol under above said conditions. By way of example, zeolites, modified zeolites, silica-alumina, alumina, silico-alumophosphates can be cited. Examples of such catalysts are cited in the above prior art.

According to an advantageous first type the dehydration catalyst is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron. Advantageously in said first embodiment the catalyst is a crystalline silicate having a ratio Si/Al of at least about 100 or a dealuminated crystalline silicate.

The crystalline silicate having a ratio Si/Al of at least about 100 is advantageously selected among the MFI and the MEL.

The crystalline silicate having a ratio Si/Al of at least about 100 and the dealuminated crystalline silicate are essentially in H-form. It means that a minor part (less than about 50%) can carry metallic compensating ions e.g. Na, Mg, Ca, La, Ni, Ce, Zn, Co.

The dealuminated crystalline silicate is advantageously such as about 10% by weight of the aluminium is removed. Such dealumination is advantageously made by a steaming optionally followed by a leaching. The crystalline silicate having a ratio Si/Al of at least about 100 can be synthesized as such or it can be prepared by dealumination of a crystalline silicate at conditions effective to obtain a ratio Si/Al of at least about 100. Such dealumination is advantageously made by a steaming optionally followed by a leaching.
The three-letter designations "MFI" and "MEL" each representing a particular crystalline silicate structure type as established by the Structure Commission of the International Zeolite Association.

Examples of a crystalline silicate of the MFI type are the synthetic zeolite ZSM-5 and silicalite and other MFI type crystalline silicates known in the art. Examples of a crystalline silicate of the MEL family are the zeolite ZSM-11 and other MEL type crystalline silicates known in the art. Other examples are Boralite D and silicalite-2 as described by the International Zeolite Association (Atlas of zeolite structure types, 1987, Butterworths). The preferred crystalline silicates have pores or channels defined by ten oxygen rings and a high silicon/aluminium atomic ratio.

Crystalline silicates are microporous crystalline inorganic polymers based on a framework of $XO_4$ tetrahedra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]: 0.53-0.56 nm and a sinusoidal channel along [100]:0.51-0.55 nm. Crystalline silicates with the MEL structure possess a bidirectional intersecting straight pore system with straight channels along [100] having pore diameters of 0.53-0.54 nm.

In this specification, the term "silicon/aluminium atomic ratio" or "silicon/aluminium ratio" is intended to mean the Si/Al atomic ratio of the overall material, which may be determined by chemical analysis. In particular, for crystalline silicate materials, the stated Si/Al ratios apply not just to the Si/Al framework of the crystalline silicate but rather to the whole material.

In a specific embodiment the catalyst preferably has a high silicon/aluminium atomic ratio, of at least about 100, preferably greater than about 150, more preferably greater than about 200, whereby the catalyst has relatively low acidity. The acidity of the catalyst can be determined by the amount of residual ammonia on the catalyst following contact of the catalyst with ammonia which adsorbs to the acid sites on the catalyst with subsequent ammonium desorption at elevated temperature measured by differential thermogravimetric analysis. Preferably, the silicon/aluminium ratio (Si/Al) ranges from about 100 to about 1000, most preferably from about 200 to about 1000. Such catalysts are known per se.

In a specific embodiment the crystalline silicate is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

In a more specific embodiment the crystalline silicate catalyst is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. The catalyst having a high silicon/aluminium atomic ratio for use in the catalytic process of the present invention is manufactured by removing aluminium from a commercially available crystalline silicate. By way of example a typical commercially available silicalite has a silicon/aluminium atomic ratio of around 120. In accordance with the present invention, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles, those particles cause partial obstruction of the pores or channels in the framework. This could inhibit the dehydration process of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed there from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate. A particularly preferred complexing agent may comprise an amine, preferably ethylene diamine tetraacetic acid (EDTA) or a salt thereof, in particular the sodium salt thereof. In a preferred embodiment, the framework silicon/aluminium ratio is increased by this process to a value of from about 150 to 1000, more preferably at least 200.

Following the aluminium leaching step, the crystalline silicate may be subsequently washed, for example with distilled water, and then dried, preferably at an elevated temperature, for example around 110° C.

Additionally, if during the preparation of the catalysts of the invention alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst is thereafter calcined, for example at a temperature of from 400 to 800° C. at atmospheric pressure for a period of from 1 to 10 hours.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicate, metal oxides such as $ZrO_2$ and/or metals, or gels including mixtures of silica and metal oxides. The binder is preferably alumina-free. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate. In mixing the catalyst with a binder, the catalyst may be formulated into pellets, extruded into other shapes, or formed into spheres or a spray-dried powder. Typically, the binder and the crystalline silicate catalyst are mixed together by a mixing process. In such a process, the binder, for example silica, in the form of a gel is mixed with the crystalline silicate catalyst material and the resultant mixture is extruded into the desired shape, for example cylindic or multi-lobe bars. Spherical shapes can be made in rotating granulators or by oil-drop technique. Small spheres can further be made by spray-drying a catalyst-binder suspension. Thereafter, the formulated crystalline silicate is calcined in air or an inert gas, typically at a temperature of from 200 to 900° C. for a period of from 1 to 48 hours. The binder preferably does not contain any aluminium compounds, such as alumina. This is because as mentioned above the preferred catalyst for use in the invention is de-aluminated to increase the silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst.

In addition, the mixing of the catalyst with the binder may be carried out either before or after the steaming and extraction steps.

According to an advantageous second type the dehydration catalyst is a crystalline silicate catalyst having a monoclinic structure, which has been produced by a process comprising providing a crystalline silicate of the MFI-type having a silicon/aluminium atomic ratio lower than 80; treating the crystalline silicate with steam and thereafter leaching aluminium from the zeolite by contact with an aqueous solution of a leachant to provide a silicon/aluminium atomic ratio in the catalyst of at least 180 whereby the catalyst has a monoclinic structure.

Preferably, in the steam treatment step the temperature is from 425 to 870° C., more preferably from 540 to 815° C., and at a water partial pressure of from 13 to 200 kPa.

Preferably, the aluminium is removed by leaching to form an aqueous soluble compound by contacting the zeolite with an aqueous solution of a complexing agent for aluminium which tends to form a soluble complex with alumina.

In accordance with this preferred process for producing monoclinic crystalline silicate, the starting crystalline silicate catalyst of the MFI-type has an orthorhombic symmetry and a relatively low silicon/aluminium atomic ratio which can have been synthesized without any organic template molecule and the final crystalline silicate catalyst has a relatively high silicon/aluminium atomic ratio and monoclinic symmetry as a result of the successive steam treatment and aluminium removal. After the aluminium removal step, the crystalline silicate may be ion exchanged with ammonium ions. It is known in the art that such MFI-type crystalline silicates exhibiting orthorhombic symmetry are in the space group Pnma. The x-ray diffraction diagram of such an orthorhombic structure has one peak at d=around 0.365 nm, d=around 0.305 nm and d=around 0.300 nm (see EP-A-0146524).

The starting crystalline silicate has a silicon/aluminium atomic ratio lower than 80. A typical ZSM-5 catalyst has 3.08 wt % $Al_2O_3$, 0.062 wt % $Na_2O$, and is 100% orthorhombic. Such a catalyst has a silicon/aluminium atomic ratio of 26.9.

The steam treatment step is carried out as explained above. The steam treatment tends to reduce the amount of tetrahedral aluminium in the crystalline silicate framework by forming alumina. The aluminium leaching or extraction step is carried out as explained above. In the aluminium leaching step, the crystalline silicate is immersed in the acidic solution or a solution containing the complexing agent and is then preferably heated, for example heated at reflux conditions (at boiling temperature with total return of condensed vapours), for an extended period of time, for example 18 hours. Following the aluminium leaching step, the crystalline silicate is subsequently washed, for example with distilled water, and then dried, preferably at an elevated temperature, for example around 110° C. Optionally, the crystalline silicate is subjected to ion exchange with ammonium ions, for example by immersing the crystalline silicate in an aqueous solution of $NH_4Cl$.

Finally, the catalyst is calcined at an elevated temperature, for example at a temperature of at least 400° C. The calcination period is typically around 3 hours.

The resultant crystalline silicate has monoclinic symmetry, being in the space group $P2_1/n$. The x-ray diffraction diagram of the monoclinic structure exhibits three doublets at d=around 0.36, 0.31 and 0.19 nm. The presence of such doublets is unique for monoclinic symmetry. More particularly, the doublet at d=around 0.36, comprises two peaks, one at d=0.362 nm and one at d=0.365 nm. In contrast, the orthorhombic structure has a single peak at d=0.365 nm.

The presence of a monoclinic structure can be quantified by comparing the x-ray diffraction line intensity at d=around 0.36 nm. When mixtures of MFI crystalline silicates with pure orthorhombic and pure monoclinic structure are prepared, the composition of the mixtures can be expressed as a monoclinicity index (in %). The x-ray diffraction patterns are recorded and the peak height at d=0.362 nm for monoclinicity and d=0.365 nm for orthorhombicity is measured and are denoted as lm and lo respectively. A linear regression line between the monoclinicity index and the lm/lo gives the relation needed to measure the monoclinicity of unknown samples. Thus the monoclinicity index %=(axlm/lo−b)×100, where a and b are regression parameters.

The such monoclinic crystalline silicate can be produced having a relatively high silicon/aluminium atomic ratio of at least 100, preferably greater than about 200 preferentially without using an organic template molecule during the crystallisation step. Furthermore, the crystallite size of the monoclinic crystalline silicate can be kept relatively low, typically less than 1 micron, more typically around 0.5 microns, since the starting crystalline silicate has low crystallite size which is not increased by the subsequent process steps. Accordingly, since the crystallite size can be kept relatively small, this can yield a corresponding increase in the activity of the catalyst. This is an advantage over known monoclinic crystalline silicate catalysts where typically the crystallite size is greater than 1 micron as they are produced in presence of an organic template molecule and directly having a high Si/Al ratio which inherently results in larger crystallites sizes.

According to an advantageous third type the dehydration catalyst is a P-modified zeolite (Phosphorus-modified zeolite). Said phosphorus modified molecular sieves can be prepared based on MFI, MOR, MEL, clinoptilolite or FER crystalline aluminosilicate molecular sieves having an initial Si/Al ratio advantageously between 4 and 500. The P-modified zeolites of this recipe can be obtained based on cheap crystalline silicates with low Si/Al ratio (below 30). By way of example said P-modified zeolite is made by a process comprising in that order:

selecting a zeolite (advantageously with Si/Al ratio between 4 and 500) among $H^+$ or $NH_4^+$-form of MFI, MEL, FER, MOR, clinoptilolite;

introducing P at conditions effective to introduce advantageously at least 0.05 wt % of P;

separation of the solid from the liquid if any;

an optional washing step or an optional drying step or an optional drying step followed by a washing step;

a calcination step;

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. No. 3,911,041, U.S. Pat. No. 5,573,990 and U.S. Pat. No. 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering. Final calcination step is performed advantageously at the temperature 400-700° C. either in a static condition or in a gas flow. Air, nitrogen or any inert gases can be used.

According to a specific embodiment of this advantageous third type the phosphorous modified zeolite is made by a process comprising in that order:

selecting a zeolite (advantageously with Si/Al ratio between 4 and 500, from 4 to 30 in a specific embodiment) among $H^+$ or $NH_4^+$-form of MFI, MEL, FER, MOR, clinoptilolite;

steaming at a temperature ranging from 400 to 870° C. for 0.01-200 h;

leaching with an aqueous acid solution at conditions effective to remove a substantial part of Al from the zeolite;

introducing P with an aqueous solution containing the source of P at conditions effective to introduce advantageously at least 0.05 wt % of P;

separation of the solid from the liquid;

an optional washing step or an optional drying step or an optional drying step followed by a washing step;

a calcination step.

Optionally between the steaming step and the leaching step there is an intermediate step such as, by way of example, contact with silica powder and drying.

Advantageously the selected MFI, MEL, FER, MOR, clinoptilolite (or H$^+$ or NH$_4^+$-form MFI, MEL, FER, MOR, clinoptilolite) has an initial atomic ratio Si/Al of 100 or lower and from 4 to 30 in a specific embodiment. The conversion to the H$^+$ or NH$_4^+$-form is known per se and is described in U.S. Pat. No. 3,911,041 and U.S. Pat. No. 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said catalyst can be used as itself as a catalyst. In another embodiment it can be formulated into a catalyst by combining with other materials that provide additional hardness or catalytic activity to the finished catalyst product. Materials which can be blended can be various inert or catalytically active materials, or various binder materials. These materials include compositions such as kaolin and other clays, various forms of rare earth metals, phosphates, alumina or alumina sol, titanic, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of catalyst which is contained in the final catalyst product ranges from 10 to 90 weight percent of the total catalyst for respectively 90 to 10 weight % of the binder, preferably 20 to 70 weight percent of the total catalyst for respectively 80 to 30 weight % of the binder.

As regards the step e) it is known in itself.

As regards the oligomerization zone, the reaction typically occurs at temperature below 250° C., preferably between 10 and 140° C. and at pressures between 0.5 and 10 Mpa. The dimerisation or oligomerisation reaction can be carried out in continuous stirred tank reactors, applying static or forced mixing, eventually equipped with pumparound systems allowing efficient removal of heat of reaction. The dimerisation or oligomerisation reaction can also be carried out in continuous tubular reactors, eventually equipped with pumparound or recycle. Depending on the catalyst applied, the dimerisation or oligomerisation reaction is carried out in a suitable solvent that contains the catalyst. In some cases the solvent can be chosen so that the olefin product do not dissolve in the same solvent and can hence be easily separated. As regards the catalyst, a review on dimerisation and oligomerisation chemistry and technologies is given in Catalysis Today, volume 14(No. 1), 10 Apr. 1992, the content of which is incorporated in the present application. The number of ethylene molecules forming the hydrocarbon chain depends on the frequency of chain transfer reactions with respect to the propagation reaction.

Higher alpha-olefins are produced by oligomerisation of ethylene either by the Ziegler process or a catalytic process. In Ziegler process alkyl aluminium reacts with ethylene in a catalytic way, resulting in a Schulz-Flory distribution or in a stoechiometric way, resulting in a Poisson distribution of alpha-olefins. The Ziegler oligomerisation can be represented by a combination of chain growth and displacement reactions that take place at an alkyl aluminium compound:

Chain growth:

Displacement:

Or

When growth and displacement occurs in the same reactor, with catalytic amounts of alkyl aluminium, a broad Schulz-Flory distribution results. When growth and displacement are separated, high quantities of alkyl aluminium are required, but results in a narrower Poisson distribution. The control of the alpha-olefin distribution is further controlled by temperature and ethylene pressure that impact the displacement rate.

Other catalysts that enable oligomerisation are based on zirconium and nickel compounds. Chain growth and displacement occur always simultaneously and hence the product distribution is a Schulz-Flory one.

Other heterogeneous catalysts that are selective for 1-hexene production are supported chromium on silica carriers that are made selective by adding pyrrol-type compounds and alkyl aluminium activators. This high selectivity is attributed to the cyclic nature of the intermediate, namely cyclohexyl-chromium compound.

As regards the isomerization of alpha olefins to internal olefins and the subsequent methathesis, in order to adjust the product distribution or to produce noneven alpha-olefins, preferentially propylene, the alpha-olefins can be isomerised into internal olefins and metathesised with ethylene into other alpha-olefins. Double bond isomerisation can be carried out with acid, basic or metallic catalysts. Typical acid catalysts are sulfonated resins, silica-alumina, supported phosphoric acid, proton-exchanged zeolites or molecular sieves, sulphated zirconia's. Typical basic catalyst are alkali or alkaline earth oxides or carbonates, supported alkali or alkaline earth oxides on alumina's, hydrotalcites, alkaline earth silicates (like xonotlites), anion exchanges resins and zinc oxide or supported zinc oxide. Typical metallic catalysts are supported palladium, cupper or nickel on alumina or silica carriers. Often these metallic isomerisation catalysts require the presence of a minimum amount of hydrogen or sulphur in the feed. In general the conversion to internal olefins is higher at lower temperature because of thermodynamic equilibrium limitations.

Metathesis of internal olefins with ethylene is performed with supported catalyst based on tungsten, molybdenum or rhenium. Typically, tungsten catalysts are supported on silica carriers whereas molybdenum and rhenium are supported on alumina based carriers.

Second Embodiment of the Invention

By comparison with the first embodiment of the invention and regarding steps a) to e), the dehydration catalyst in said second embodiment is restricted to the group consisting of a crystalline silicate having a ratio Si/Al of at least about 100, a dealuminated crystalline silicate, and a phosphorus modified zeolite. The dehydration catalyst of said second embodiment is the advantageous dehydration catalyst of the first embodiment of the invention. Operating conditions of said second embodiment and regarding steps a) to e), are already described in the first embodiment of the invention.

As regards the dimerization zone, a review on dimerisation and oligomerisation chemistry and technologies is given in Catalysis Today, volume 14(No. 1), 10 Apr. 1992. The number of ethylene molecules forming the hydrocarbon chain depends on the frequency of chain transfer reactions with respect to the propagation reaction. In case of dimerisation the propagation step needs to minimised. This can be done by maximising the chain transfer by working at high temperature and by working at high ethylene concentration in order to prevent codimerisation of the formed 1-butene with ethylene. Also the catalyst plays an essential role. Typical dimerisation catalysts are titanium or nickel compounds activated with alkyl aluminium compounds. It is general accepted that the Ti(IV) valency has to be stabilised by selecting the appropriate ligands, alkyl aluminium compound, the solvent polarity and the Al/Ti ratio. By selecting the appropriate ligands and alkyl aluminium compound, the dimerisation occurs by the formation of an intermediate cyclopentane-titanium complex that decomposes into 1-butene by intermolecular hydride transfer. The absence of hydride on the catalytic centre ensures that no double bond isomerisation into 2-butene occurs. Nickel compounds that can catalyse the selective production of butenes are typically based on cationic nickel salts, stabilised with phosphine and activated with alkyl aluminium compounds. The relative presence of the different compounds and the use of particular solvents or acidic additive determines whether the catalyst exhibits double bond isomerisation activity: under appropriate conditions high 2-butene/1-butene ratios can be obtained.

As regards the isomerization of 1-butene and the subsequent methathesis, catalysts and operating conditions cited in the first embodiment can be used. The metathesis reaction of butenes with ethylene over a metathesis catalyst to produce propylene, is favored where the butenes are in the form of 2-butenes rather than 1-butenes. The metathesis of 2-butene with ethylene results in propylene:

This metathesis reaction is an equilibrium reaction and the overall conversion can be optimised by recycling non-converted 2-butene and ethylene. Thus, in accordance with a preferred embodiment, and as described in greater detail below, the 1-butene stream recovered at step h) is passed to an isomerization zone l) for isomerizing at least a portion of the quantity of 1-butenes therein contained to form an isomerized stream comprising an increased quantity of 2-butenes.

As will be appreciated, such isomerization of 1-butenes to 2-butenes can desirably occur over a suitable isomerization catalyst at selected appropriate isomerization reaction conditions. The 1-butene to 2-butene isomerization reaction is actually a hydroisomerization as it is generally conducted in the presence of a hydrogen atmosphere to facilitate the double bond migration, but such that the use of hydrogen is minimized to avoid undesirable hydrogenation side reactions. The catalysts typically employed in such processing are commonly based on noble metals (palladium, rhodium, platinum, etc.) deposited on an inert alumina support; palladium is normally preferred. Typical or usual reaction conditions may involve a temperature of about 20° to 200° C. and typically a pressure of about 1.0 to 4.0 MPa. The feed to the hydroisomerization reactor is usually preheated by exchange with the reactor effluent and by steam. Such a heated feed then enters the reactor, which typically operates in a mixed phase with one or more catalyst beds. After cooling, the isomerization products are typically flashed to remove excess hydrogen gas. The reaction temperature is generally chosen so as to maximize conversion to 2-butene (favored by lower temperatures) while still having a reasonable rate of reaction; hence it is commonly desirable to operate at a temperature of less than 150° C. Desirably, the isomerized stream will contain 2-butene and 1-butene in a molar ratio of at least 8, e.g., at least 8 moles of 2-butene per mole of 1-butene, and, in accordance with at least certain preferred embodiments a molar ratio of greater than 10, e.g., more than 10 moles of 2-butene per mole of 1-butene. If fractionated, the residual 1-butene (lighter than 2-butene) can be recycled to the isomerization reactor.

The metathesis reaction can generally be carried out under conditions and employs catalysts such as are known in the art. In accordance with one preferred embodiment, a metathesis catalyst such as containing a catalytic amount of at least one of molybdenum oxide and tungsten oxide is suitable for the metathesis reaction. Conditions for the metathesis reaction generally include reaction temperature ranging from about 20° to about 450° C., preferably 250° to 350° C., and pressures varying from about atmospheric to upwards of 4.0 MPa, preferably between 1.0 and 3.0 MPa, although higher pressures can be employed if desired. Catalysts which are active for the metathesis of olefins and which can be used in the process of this invention are of a generally known type. In this regard, reference is made to "Journal of Molecular Catalysis", 28 (1984) pages 117-131, to "Journal of Catalysis", 13 (1969)

pages 99-113, to "Applied Catalysis" 10 (1984) pages 29-229 and to "Catalysis Reviews", 3 (1) 1969) pages 37-60. The disproportionation (metathesis) of 2-butene with ethylene can, for example, be carried out in the vapor phase at about 300° to 350° C. and about 0.5 MPa absolute (75 psia) with a WHSV of 50 to 100 and a once-through conversion of about 15%, depending on the ethylene to 2-butene ratio.

Such metathesis catalysts may be homogeneous or heterogeneous, with heterogeneous catalysts being preferred. The metathesis catalyst preferably comprises a catalytically effective amount of transition metal component. The preferred transition metals for use in the present invention include tungsten, molybdenum, nickel, rhenium, and mixtures thereof. The transition metal component may be present as elemental metal and/or one or more compounds of the metal. If the catalyst is heterogeneous, it is preferred that the transition metal component be associated with a support. Any suitable support material may be employed provided that it does not substantially interfere with the feedstock components or the lower olefin component conversion. Preferably, the support material is an oxide, such as silica, alumina, titania, zirconia and mixtures thereof. Silica is a particularly preferred support material. If a support material is employed, the amount of transition metal component used in combination with the support material may vary widely depending, for example, on the particular application involved and/or the transition metal being used. Preferably, the transition metal comprises about 1% to about 20%, by weight (calculated as elemental metal) of the total catalyst. The metathesis catalyst may advantageously comprise a catalytically effective amount of at least one of the above-noted transition metals, and are capable of promoting olefin metathesis. The catalyst may also contain at least one activating agent present in an amount to improve the effectiveness of the catalyst. Various activating agents may be employed, including activating agents which are well known in the art to facilitate metathesis reactions. Light olefin metathesis catalysts can, for example, desirably be complexes of tungsten (W), molybdenum (Mo), or rhenium (Re) in a heterogeneous or homogeneous phase.

In general, the metathesis equilibrium for propylene production is also favored by lower temperatures and higher (ethylene/2-butene) ratios. For example, at a temperature of 600° K, the metathesis equilibria shown in the following Table, below, can be established:

| ethylene/2-butene ratio | 2-butene converted |
|---|---|
| 1 | 65 |
| 2 | 83 |
| 3 | 89 |

Third Embodiment of the Invention

By comparison with the second embodiment of the invention the difference is the dimerization to 2-butene in step g) instead of dimerization to 1-butene. Operating conditions of said third embodiment are the same as in the second embodiment.

EXAMPLES

Figure 1:
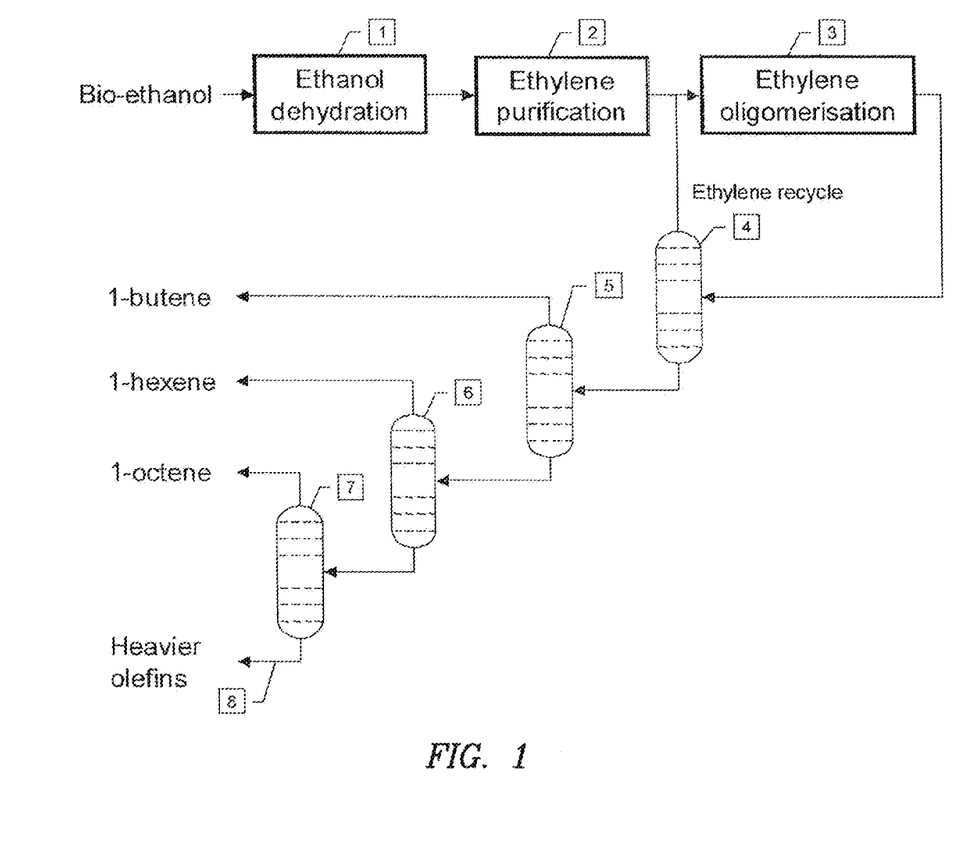

FIG. 1:
Ethanol from biological origin is sent to a dehydration reactor (1) and subsequently the ethylene is purified (2). The ethylene is next oligomerised (3) into a mixture of alpha-olefins having from 4 to more than 20 carbons. The non-converted ethylene is recycled back (4) to the oligomerisation reactor (3). The alpha-olefins are separated in a series of distillation towers producing as overhead product 1-butene (5), 1-hexene (6), 1-octene (7) and higher alpha-olefins (8). These alpha-olefins can be utilised for poly-ethylene production, poly-1-butene, poly-alpha-olefins (PAO's), detergent alcohols, linear alkyl benzenes (LAB).

Figure 2:
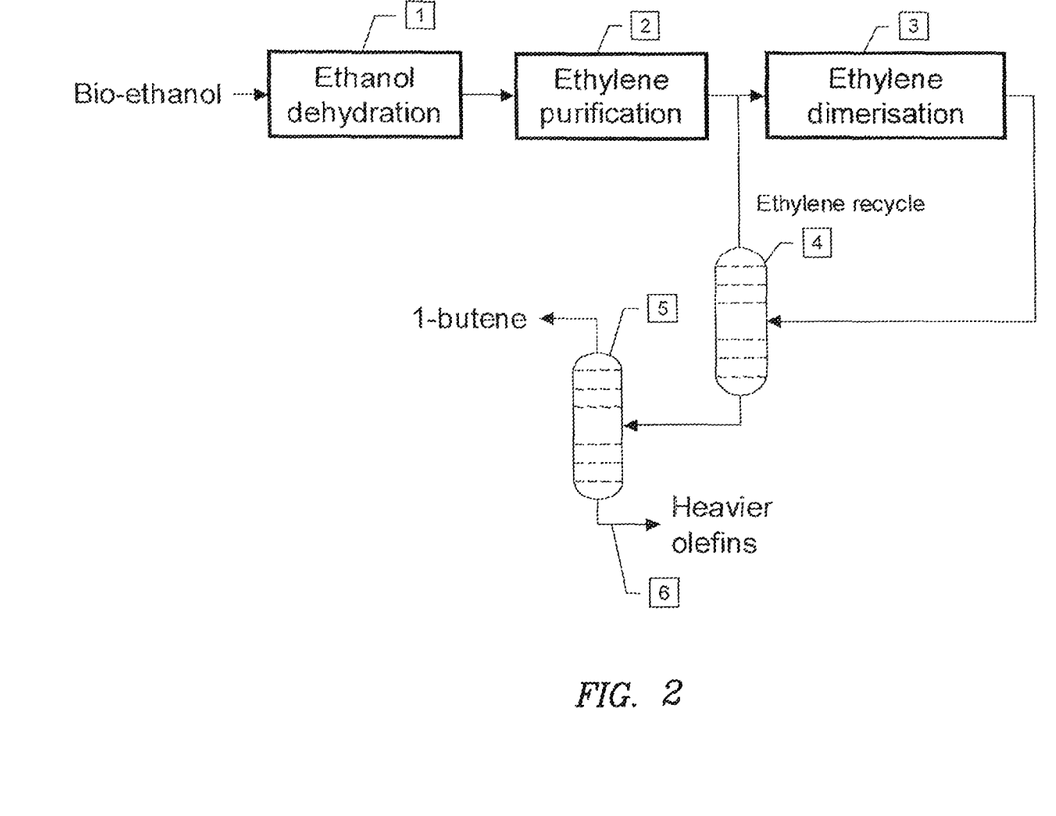

FIG. 2:
Ethanol from biological origin is sent to a dehydration reactor (1) and subsequently the ethylene is purified (2). The ethylene is next dimerised (3) into 1-butene. The non-converted ethylene is recycled back (4) to the dimerisation reactor (3). The 1-butene is separated in a distillation tower producing as overhead product 1-butene (5) and heavier products as bottom product (6). This 1-butene can be utilised for poly-ethylene production and poly-1-butene.

Figure 3:
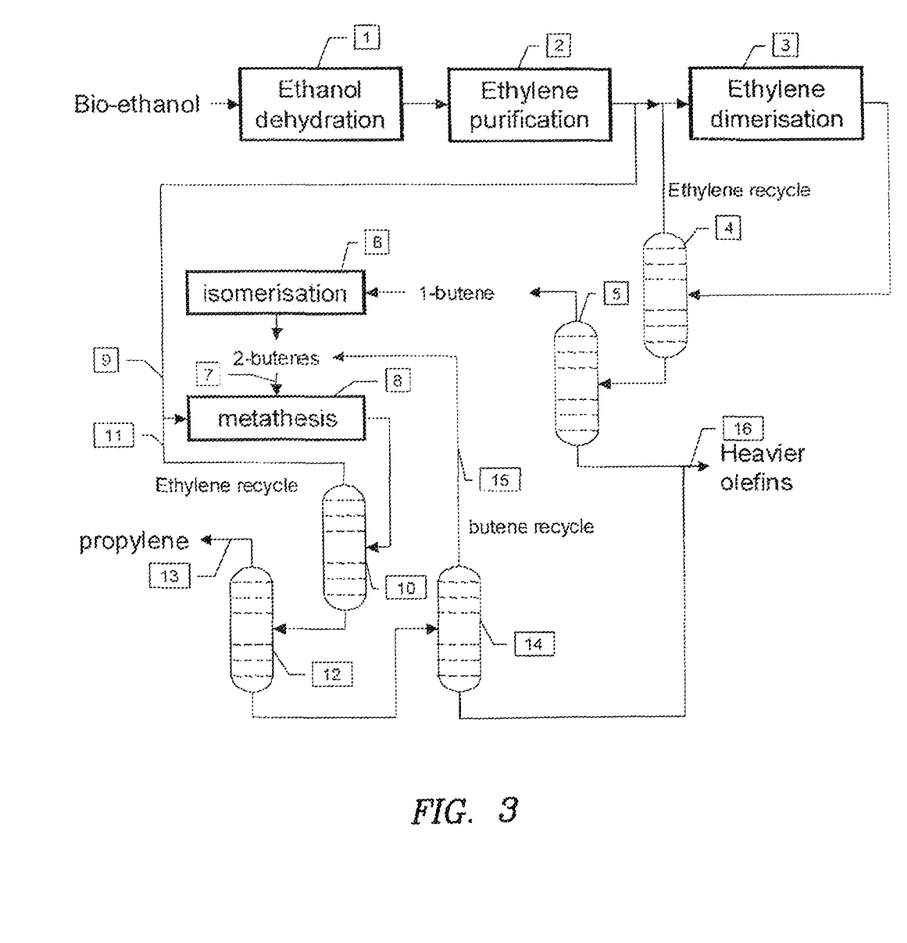

FIG. 3:
Ethanol from biological origin is sent to a dehydration reactor (1) and subsequently the ethylene is purified (2). The ethylene is next dimerised (3) into 1-butene. The non-converted ethylene is recycled back (4) from the de-ethaniser to the dimerisation reactor (3). The 1-butene is separated in a distillation tower producing as overhead product 1-butene (5) and heavier products as bottom product (16). The 1-butene is sent to an isomerisation reaction (6) where a mixture of 2-butenes and 1-butene is produced. This mixture (7) is sent together with ethylene (9) to the metathesis reactor (8). The product olefins are sent to a de-ethaniser (10) where the ethylene is recovered overhead and recycled (11) to the metathesis reaction (8). The bottom product is sent to the de-propaniser (12) where the propylene is recovered overhead (13). The bottom product of the de-propaniser flows to the de-butaniser (14) that recycles the non-converted butenes (15) back to the metathesis section (8). The bottom product, consisting of heavies is purged out of the process (16).

Figure 4:
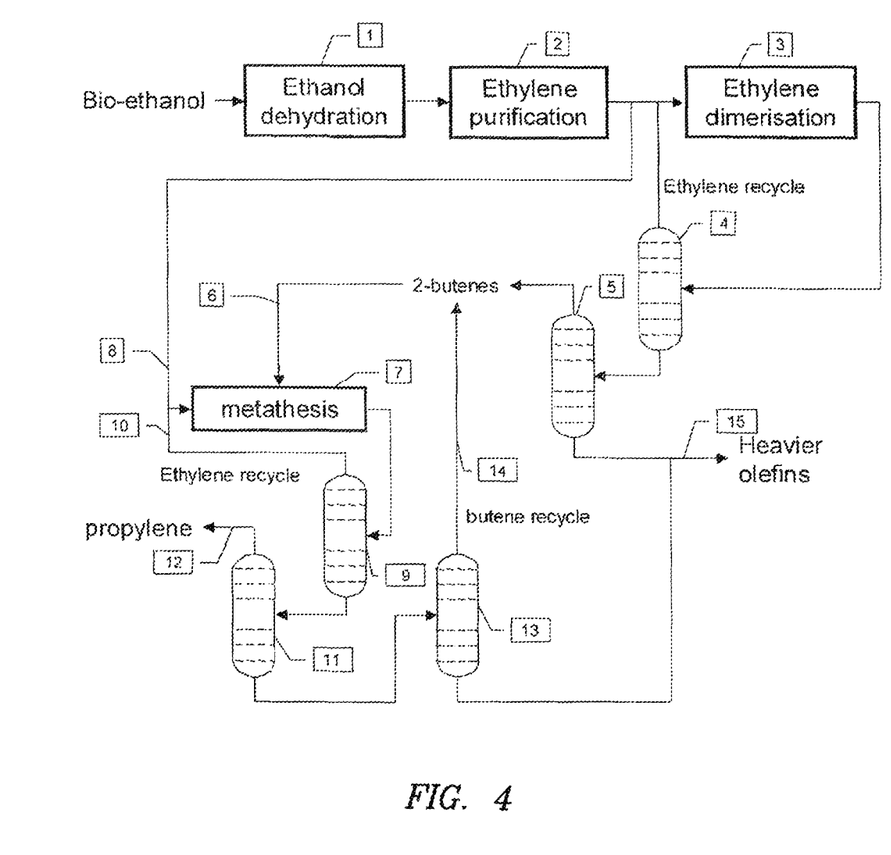

FIG. 4:
Ethanol from biological origin is sent to a dehydration reactor (1) and subsequently the ethylene is purified (2). The ethylene is next dimerised (3) with a appropriate catalyst that shifts the double bond at the same time into substantially 2-butenes. The non-converted ethylene is recycled back (4) from the de-ethaniser to the dimerisation reactor (3). The 2-butenes are separated in a distillation tower (5) producing as overhead product substantially 2-butenes (6) and heavier products as bottom product (16). The 2-butenes are sent (6) together with ethylene (8) to the metathesis reactor (7). The product olefins are sent to a de-ethaniser (9) where the ethylene is recovered overhead and recycled (10) to the metathesis reaction (7). The bottom product is sent to the de-propaniser (11) where the propylene is recovered overhead (12). The bottom product of the de-propaniser flows to the de-butaniser (13) that recycles the non-converted butenes (14) back to the metathesis reactor (7). The bottom product, consisting of heavies is purged out of the process (15).

Figure 5:
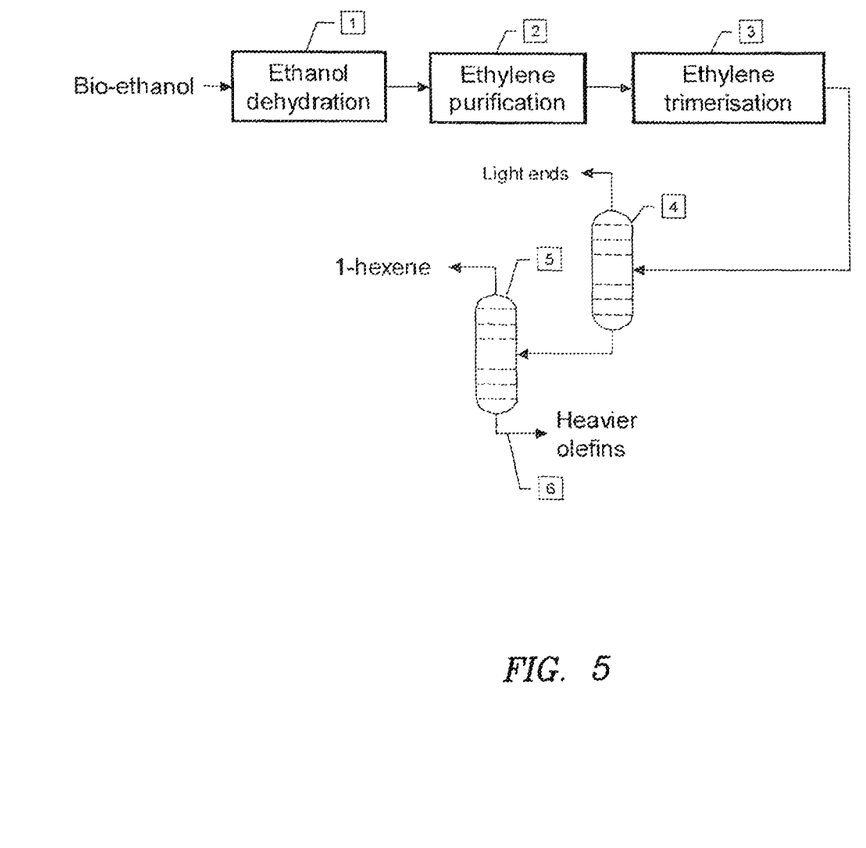

FIG. 5:
Ethanol from biological origin is sent to a dehydration reactor (1) and subsequently the ethylene is purified (2). The ethylene is next trimerised (3) into 1-hexene. The light-ends are removed overhead of a first distillation tower (4), optionally the non-converted ethylene can be extracted from the light-ends and recycled back to the dimerisation reactor (3). The 1-hexene is separated in a distillation tower producing as overhead product 1-hexene (5) and heavier products as bottom product (6). This 1-hexene can be utilised for poly-ethylene production.

What is claimed is:

1. A process to make alpha olefins comprising:
a) providing a dehydration zone containing a dehydration catalyst,
b) introducing a feedstock comprising ethanol, water, and an inert component into said dehydration zone and into contact with said dehydration catalyst,
c) operating said dehydration zone at conditions effective to dehydrate at least a portion of the ethanol to an effluent consisting essentially of ethylene, water, unconverted ethanol if any, and the inert component,
d) introducing said effluent into a first fractionation zone to recover an ethylene stream,
e) introducing said ethylene stream into an oligomerization zone containing an oligomerization catalyst and into contact with said oligomerization catalyst,
f) operating said oligomerization zone at conditions effective to produce an effluent consisting essentially of 1-butene, 1-hexene, heavier alpha olefins having 8 carbons or more, and unconverted ethylene if any,
g) introducing the effluent from step h) into a second fractionation zone to recover a stream consisting essentially of 1-butene, a stream consisting essentially of 1-hexene, a stream consisting essentially of heavier alpha olefins having 8 carbons or more and a stream consisting essentially of ethylene,
h) combining the 1-hexene and at least one heavier alpha olefin having 8 carbons or more recovered at step g) and isomerizing the combined stream to produce an internal olefin and
i) converting the effluent recovered at step h) by metathesis with the ethylene into different alpha-olefins with an even or odd number of carbons.

2. The process according to claim 1 wherein the oligomerization of step f) is operated at conditions effective to produce an effluent consisting essentially of 1-butene, 1-hexene, 1-octene, heavier alpha olefins having 10 carbons or more, and unconverted ethylene if any, and wherein in step g), a stream consisting essentially of 1-butene, a stream consisting essentially of 1-hexene, a stream consisting essentially of 1-octene, a stream consisting essentially of heavier alpha olefins having 10 carbons or more, and a stream consisting essentially of ethylene are recovered.

3. The process according to claim 1 wherein the dehydration catalyst is selected from the group consisting of a crystalline silicate having a ratio Si/Al of at least about 100, a dealuminated crystalline silicate, and a phosphorus modified zeolite.

4. The process according to claim 1 wherein the ethylene stream recovered at step g) is recycled back to the oligomerization zone of step f).

5. The process according to claim 1 wherein the 1-hexene recovered at step g) is isomerized to 2-hexene.

6. A process to make alpha olefins comprising:
a) providing a dehydration zone containing a dehydration catalyst selected from the group consisting of a crystalline silicate having a ratio Si/Al of at least about 100, a dealuminated crystalline silicate, and a phosphorus modified zeolite,
b) introducing a feedstock comprising ethanol, water, and an inert component into said dehydration zone and into contact with said dehydration catalyst,
c) operating said dehydration zone at conditions effective to dehydrate at least a portion of the ethanol to an effluent consisting essentially of ethylene, water, unconverted ethanol if any, and the inert component,
d) introducing said effluent into a first fractionation zone to recover an ethylene stream,
e) introducing said ethylene stream into an dimerization zone containing an dimerization catalyst and into contact with said dimerization catalyst,
f) operating said dimerization zone at conditions effective to produce an effluent consisting essentially of 1-butene, heavier alpha olefins having 8 carbons or more, and unconverted ethylene if any,
g) introducing the effluent from step g) into a second fractionation zone to recover a stream consisting essentially of 1-butene, a stream consisting essentially of heavier olefins having 8 carbons or more, and a stream consisting essentially of ethylene,
h) combining at least one of the heavier olefins having 8 carbons or more recovered at step g) and isomerizing the combined stream to produce an internal olefin and
i) converting the effluent recovered at step h) by metathesis with the ethylene into different alpha-olefins with an even or odd number of carbons.

7. The process according to claim 6 wherein the ethylene stream recovered at step g) is recycled back to the dimerization zone of step f).

8. The process according to claim 6 further comprising:
j) a isomerizing the stream consisting essentially of 1-butene recovered at step h) to a stream comprising an increased quantity of 2-butene,
k) introducing the stream comprising the increased quantity of 2-butene into a methathesis zone containing a methathesis catalyst and into contact simultaneously with ethylene and said methathesis catalyst, wherein, the methathesis zone is operated at conditions effective to produce propylene,
l) introducing the effluent of step j) into a third fractionation zone to recover propylene, unreacted ethylene, unreacted 2-butene, and heavier components, 1) optionally recycling the unreacted ethylene and unreacted 2-butene to the methathesis zone.

9. A process to make alpha olefins comprising:
a) providing a dehydration zone containing a dehydration catalyst selected from the group consisting of a crystalline silicate having a ratio Si/Al of at least about 100, a dealuminated crystalline silicate, and a phosphorus modified zeolite,
b) introducing a feedstock comprising ethanol, water, and an inert component into said dehydration zone and into contact with said dehydration catalyst,
c) operating said dehydration zone at conditions effective to dehydrate at least a portion of the ethanol to an effluent consisting essentially of ethylene, water, unconverted ethanol if any, and the inert component,
d) introducing said effluent into a first fractionation zone to recover an ethylene stream
e) introducing said ethylene stream into an dimerization zone containing an dimerization catalyst and into contact with said dimerization catalyst,
f) operating said dimerization zone at conditions effective to produce an effluent consisting essentially of 2-butene, heavier alpha olefins having 8 carbons or more, and unconverted ethylene if any,
g) introducing the effluent from step g) into a second fractionation zone to recover a stream consisting essentially of 2-butene, a stream consisting essentially of heavier olefins having 8 carbons or more, and a stream consisting essentially of ethylene, h) combining at least one of the heavier olefins having 8 carbons or more recovered at step g) and isomerizing the combined stream to produce an internal olefin and i) converting the effluent recovered at step h) by metathesis with the ethylene into different alpha-olefins with an even or odd number of carbons.

10. The process according to claim 9 wherein the ethylene stream recovered at step g) is recycled back to the dimerization zone of step f).

11. The process according to claim 9 further comprising:

j) a introducing said 2-butene into a methathesis zone containing a methathesis catalyst and into contact simultaneously with ethylene and said methathesis catalyst, wherein, the methathesis zone is operated at conditions effective to produce propylene, k) introducing the effluent of step i) into a third fractionation zone to recover propylene, unreacted ethylene, unreacted 2-butene, and heavier components, l) a optionally recycling the unreacted ethylene and unreacted 2-butene to the methathesis zone.

12. A process to make alpha olefins comprising:

a) providing a dehydration zone containing a dehydration catalyst selected from the group consisting of a crystalline silicate having a ratio Si/Al of at least about 100, a dealuminated crystalline silicate, and a phosphorus modified zeolite, b) introducing a feedstock comprising ethanol, water, and an inert component into said dehydration zone and into contact with said dehydration catalyst, c) operating said dehydration zone at conditions effective to dehydrate at least a portion of the ethanol to an effluent consisting essentially of ethylene, water, unconverted ethanol if any, and the inert component, d) introducing said effluent into a first fractionation zone to recover an ethylene stream, e) introducing said ethylene stream into an trimerization zone containing an trimerization catalyst and into contact with said trimerization catalyst, f) operating said trimerization zone at conditions effective to produce an effluent consisting essentially of 1-hexene, light ends, heavier alpha olefins having 8 carbons or more, and unconverted ethylene if any, g) introducing the effluent from step g) into a second fractionation zone to recover a stream consisting essentially of 1-hexene, a stream consisting essentially of heavier olefins having 8 carbons or more, and a stream consisting essentially of ethylene, h) combining at least one of the heavier olefins having 8 carbons or more recovered at step g) and isomerizing the combined stream to produce an internal olefin and i) converting the effluent recovered at step h) by metathesis with the ethylene into different alpha-olefins with an even or odd number of carbons.

13. The process according to claim 1 wherein the ethanol is from biological origin.

14. The process according to claim 8 wherein the ethanol is from biological origin.

15. The process according to claim 1, wherein the dehydration catalyst is a crystalline silicate having a ratio Si/Al of at least about 100 that is silicalite-1, boralite C, TS-1, an MEL, an FER, an MTT, an MWW, a TON, an EUO, an MFS, or a ZSM-48.

16. The process according to claim 1, wherein the dehydration catalyst is a dealuminated crystalline silicate that is silicalite-1, boralite C, TS-1, an MEL, an FER, an MTT, an MWW, a TON, an EUO, an MFS, or a ZSM-48.

17. The process according to claim 1, wherein the dehydration catalyst is a phosphorus modified zeolite that is silicalite-1, boralite C, TS-1, an MOR, an MEL, a clinoptilolite, or an FER.

18. The process according to claim 1, wherein the dehydration catalyst is an MFI crystalline silicate having a monoclinic structure and a Si/Al ratio of at least 180.

19. The process according to claim 1, wherein the effluent recovered from step d) consists essentially of the ethylene, water, unconverted ethanol if any, and the inert component, and does not comprise acetylene.

20. The process according to claim 5 wherein the 2-hexene is subsequently transformed by metathesis with the aid of additional ethylene into 1-pentene and propylene.

21. The process according to claim 1, wherein the 1-hexene and the at least one heavier alpha olefin having 8 carbons or more recovered at step g) are isomerized in the presence of:

an acid catalyst comprising a sulfonated resin, a supported phosphoric acid, or a sulphated zirconia;

a basic catalyst; or a metallic catalyst comprising palladium, cupper or nickel supported on an alumina or silica carrier.

* * * * *